US010844343B2

(12) United States Patent
Hollah et al.

(10) Patent No.: US 10,844,343 B2
(45) Date of Patent: Nov. 24, 2020

(54) DEVICE FOR THE ELECTRICAL DISINTEGRATION OF CELL STRUCTURES, AND INSTALLATION AND USE OF THE DEVICE FOR PRODUCING FEED INTERMEDIATES AND FEED PRODUCTS

(71) Applicant: Hugo Vogelsang Maschinenbau GmbH, Essen (DE)

(72) Inventors: Clemens Hollah, Lastrup (DE); Paul Krampe, Essen/Olbg. (DE); Andreas Fastenau, Cloppenburg (DE)

(73) Assignee: Hugo Vogelsang Maschinenbau GmbH, Essen (DE)

( * ) Notice: Subject to any disclaimer, the term of this patent is extended or adjusted under 35 U.S.C. 154(b) by 502 days.

(21) Appl. No.: 15/540,584

(22) PCT Filed: Jan. 15, 2016

(86) PCT No.: PCT/EP2016/050724
§ 371 (c)(1),
(2) Date: Jun. 29, 2017

(87) PCT Pub. No.: WO2016/116357
PCT Pub. Date: Jul. 28, 2016

(65) Prior Publication Data
US 2018/0016541 A1 Jan. 18, 2018

(30) Foreign Application Priority Data
Jan. 21, 2015 (DE) .................... 20 2015 000 482 U

(51) Int. Cl.
*C12M 1/33* (2006.01)
*C12M 1/42* (2006.01)
(Continued)

(52) U.S. Cl.
CPC .......... *C12M 45/02* (2013.01); *C12M 21/04* (2013.01); *C12M 23/42* (2013.01); *C12M 33/16* (2013.01);
(Continued)

(58) Field of Classification Search
CPC ....... C12M 33/16; C12M 35/02; C12M 45/07
See application file for complete search history.

(56) References Cited

U.S. PATENT DOCUMENTS 4,718,337 A * 1/1988 Wiederkehr ............ B30B 9/163
100/75
4,898,092 A 2/1990 Greer
(Continued)

FOREIGN PATENT DOCUMENTS

DE 3538194 A1 6/1987
DE 19752961 C1 7/1999
(Continued)

OTHER PUBLICATIONS

Ngadi et al. "Pulsed electric field assisted juice extraction." Stewart Postharvest Review, vol. 4 (2006), No. 2, pp. 1-8. (Year: 2006).*
(Continued)

*Primary Examiner* — William H. Beisner
(74) *Attorney, Agent, or Firm* — Kilpatrick Townsend & Stockton LLP; Dean W. Russell; Melissa L. Love

(57) ABSTRACT

Disclosed is a device for the electrical disintegration of cell structures including a chamber having an inlet for receiving material containing cell structures, an outlet for the discharge thereof, and a conveyor line extending between the inlet and the outlet, an electrode unit which has an electrode body which is arranged within the chamber at least portionwise along the conveyor line, wherein the chamber has a wall which is portion-wise or completely electrically conductive and electrically insulated from the electrode body,
(Continued)

Figure 1:
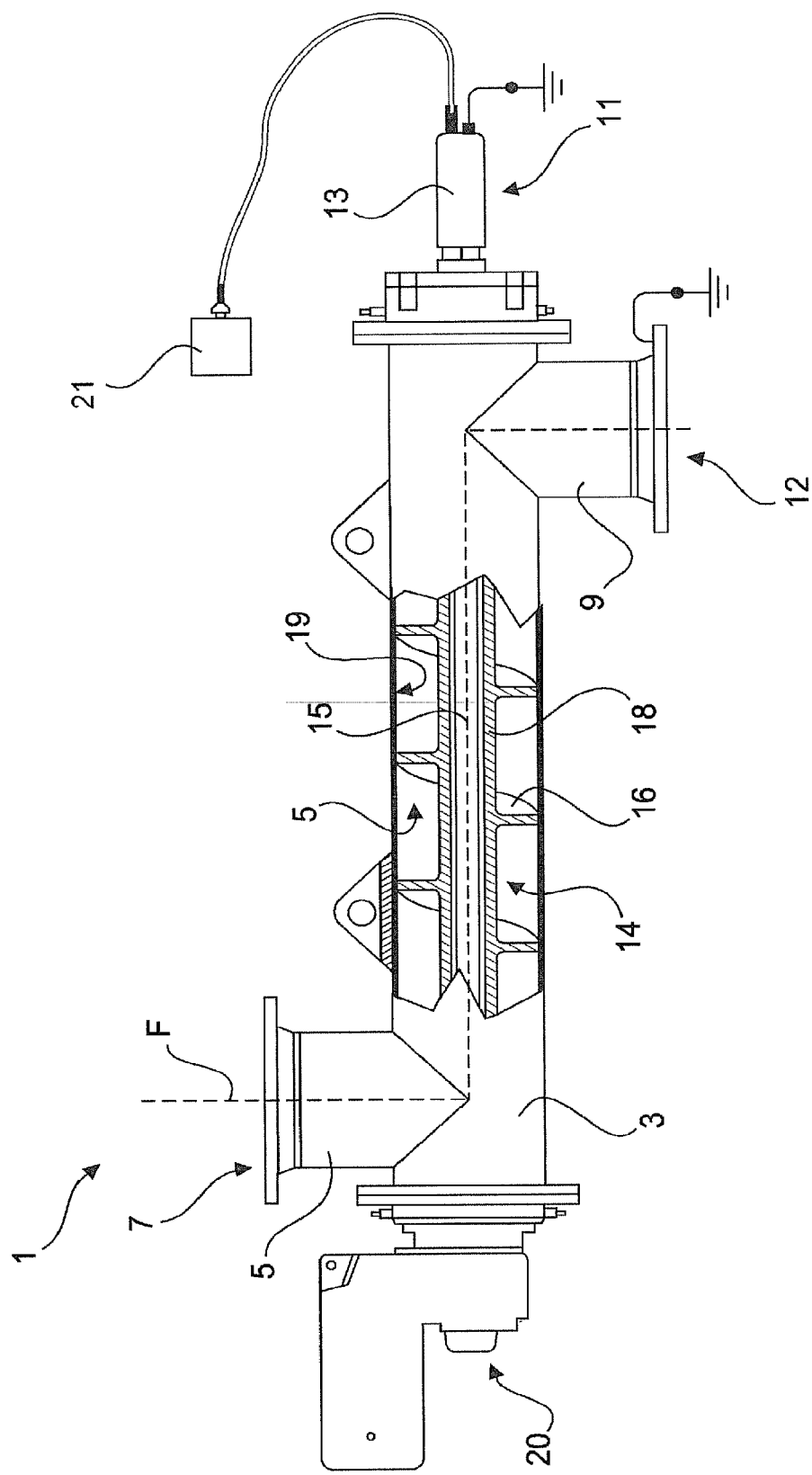

and the electrode unit is adapted to generate an electric field between the electrode body and the wall for electrical disintegration.

19 Claims, 2 Drawing Sheets

(51) Int. Cl.
    *C12M 3/00*     (2006.01)
    *C12M 1/26*     (2006.01)
    *C12M 1/00*     (2006.01)
    *C12M 1/107*     (2006.01)

(52) U.S. Cl.
    CPC ............ *C12M 35/02* (2013.01); *C12M 35/04* (2013.01); *C12M 45/07* (2013.01); *C12M 45/20* (2013.01)

(56) References Cited

U.S. PATENT DOCUMENTS

| | | | | |
|---|---|---|---|---|
| 5,403,455 A | * | 4/1995 | Candor | ................. B01D 61/56 204/515 |
| 6,035,546 A | * | 3/2000 | Stricker | .................... B01J 8/10 34/147 |
| 2002/0140333 A1 | * | 10/2002 | Kato | ...................... H01T 13/36 313/143 |
| 2010/0317053 A1 | | 12/2010 | Stromberg et al. | |

FOREIGN PATENT DOCUMENTS

| | | |
|---|---|---|
| DE | 19913514 C1 | 10/2000 |
| DE | 102008033049 A1 | 1/2010 |
| DE | 202011004177 U1 | 6/2012 |
| DE | 202011107866 U1 | 2/2013 |
| DE | 202013001124 U1 | 5/2014 |
| DE | 202013005125 U1 | 9/2014 |
| EP | 2792739 A1 | 10/2014 |
| GB | 1011891 | 12/1965 |
| JP | S61-063248 A | 4/1986 |
| JP | H02-027974 A | 1/1990 |
| JP | 05039308 A * | 2/1993 |
| JP | 2000-507685 A | 6/2000 |
| SU | 679196 | 8/1979 |
| WO | 1984000378 A1 | 2/1984 |
| WO | 2011147601 A1 | 12/2011 |
| WO | 2014186670 A2 | 11/2014 |

OTHER PUBLICATIONS

International Patent Application No. PCT/EP2016/050724, International Search Report (including English translation) and Written Opinion, dated Mar. 22, 2016.
Japanese Patent Application No. 2017-538398, Office Action dated Sep. 5, 2018.
International Patent Application No. PCT/EP2016/050724, Written Opinion of the International Searching Authority (including English translation), dated Mar. 22, 2016.
International Patent Application No. PCT/EP2016/050724, International Preliminary Report on Patentability, dated Jul. 25, 2017.
Brazilian Application No. BR 112017014307-0, "Office Action," dated Nov. 12, 2019, 5 pages.

* cited by examiner

DEVICE FOR THE ELECTRICAL DISINTEGRATION OF CELL STRUCTURES, AND INSTALLATION AND USE OF THE DEVICE FOR PRODUCING FEED INTERMEDIATES AND FEED PRODUCTS

CROSS REFERENCE TO RELATED APPLICATIONS

This patent application is the U.S. national stage entry of PCT/EP2016/050724 ("the '724 application"), filed on Jan. 15, 2016, which application is related to and claims priority benefits from German Application No. 20 2015 000 482.2 ("the '482 application"), filed on Jan. 21, 2015. The '724 and '482 applications are hereby incorporated in their entireties by this reference.

The present invention concerns a device for the electrical disintegration of cell structures, comprising a chamber having an inlet for receiving material containing cell structures, an outlet for the discharge thereof, and a conveyor line extending between the inlet and the outlet, an electrode unit which has an electrode body which is arranged within the chamber at least portion-wise along the conveyor line, wherein the chamber has a wall which is portion-wise or completely electrically conductive and electrically insulated from the electrode body, and the electrode unit is adapted to generate an electric field between the electrode body and the wall for electrical disintegration.

Devices of the above-indicated kind, for example known from DE 20 2013 001 124.6 or DE 20 2011 004 177 U1, are used in different areas, primarily for the treatment of cell structures and/or material containing cells. A previous area of use was in particular the area of biogas installations and sewage treatment installations. The aim is basically to improve the processability of the material containing cell structures by means of disintegration of the cell structures. In the case of biogas installations and sewage treatment installations disintegration serves for example to promote the generation of biogas.

In general chemical reactions of the cell structures or the molecules forming the cells are promoted by so-called cracking of the cell structures.

The term disintegration is used generally to mean the comminution and break-up or pulping of cells or cell structures under the action of external forces.

Electrical disintegration is based on the operating principle of exposing cell structures to an electric field which occurs between two electrodes. As a consequence of the action of the electric field on the cells and the cell structures charge displacements occur at the cell membranes. In the known installations for electrical disintegration use is then made in that respect of the fact that the cells and cell structures move within the chamber in which the electric field is produced. Due to the movement of the cells and cell structures the field strength influencing them changes locally in relation to their respective cell membrane. Due to that lasting change the cell membrane and/or the cell structure is exposed to vibrations or gravitational forces, leading to destabilisation. With sufficiently strong simulation the cell structure is loosened up or dispersed. With a greater degree of influence the cell membranes are collapsed. The latter is known by the term electroporation. The effect of that disintegration is that the availability in particular of nutrients from the cell structures is enhanced. In this connection reference is made to the above-mentioned breakup. For example in the case of grain as a feed for animals, for example piglets, improved disintegration has an advantageous effect on the feed exploitation by the animals.

Enhancing the availability of nutrients in a material is consequently of great significance not only in the case of biogas installations but in particular also in the feed industry. It is known for example from DE 199 13 514 C1 to break up a raw material, for example whole grain, by means of thermal and mechanical treatment in order to make nutrients contained therein more easily accessible in an intermediate product to be produced or the finished feed product. The aim in the area of the feed industry is to increase in particular digestibility, palatability and above all usability of the feed so that it is possible to achieve greater increases in weight in the case of animals, with a lower level of feed use. As the animal husbandry and meat processing industry is subjected to cost pressures to a high degree there is a need for feed production that is as efficient as possible in order to achieve high growth rates in the case of the animals consuming the feed, in the shortest possible time and with the lowest possible level of resource use. In addition the number of pathogenic germs in the feed could be reduced to a minimum.

Therefore the object of the invention was to improve a device of the kind set forth in the opening part of this specification, such that it allows efficiency-increasing use in the production of feed intermediate and finished feed products.

In a device of the kind set forth in the opening part of this specification, that object is attained by the invention in that a conveyor screw for conveying the material is drivably arranged in the conveyor line, wherein the electrode body is accommodated in a cavity in the conveyor screw. The invention makes use of the realisation that the device identified in the opening part of this specification can be successfully used not only in biogas installations but also for the electrical disintegration of cell structures in pourable material like for example whole grain. Unlike the case with fluid material like biomass, the disintegration of cell structures in a basically solid, pourable material is however more difficult. The invention pursues the approach of ensuring a well controlled transport, which can be exactly adjusted in terms of the conveyor speed, of the material containing cell structures, through the chamber of the disintegration device, by means of the conveyor screw. By means of the conveyor screw which is preferably motor-drivable, it is possible in accordance with the invention to exactly meter the residence time of the material containing cell structures in the chamber for electrical disintegration. Because the conveyor screw accommodates the electrode body of the electrode unit in a cavity in itself, transport of the material containing cell structures is further ensured, which is not impeded by the electrode itself. The arrangement is also compact so that long conveyor lines or many parallel devices for electrical disintegration can be set up on a very small footprint area in industrial manufacturing installations.

In a preferred embodiment the conveyor screw has a hollow shaft and the electrode body is arrange coaxially with the conveyor screw in the hollow shaft.

Further preferably the conveyor screw partially or completely comprises an electrically non-conductive material. That has the advantage that the conveyor screw itself causes no or at any event only a reduced adverse effect in terms of field propagation in the chamber between the electrode and the chamber wall. That in turn has a positive effect on the efficiency of electrical disintegration.

In a preferred configuration the electrically non-conductive material is an electrically non-conductive, preferably organic, polymer. Particularly preferably that polymer is selected as a thermosetting material, for example polyurethane, elastomer, for example hard rubber, or in the form of a plastomer, for example polycarbonate, or a combination of a plurality of polymers. Thermoplastic materials like for example polypropylene are also preferred.

It is also preferred if the electrically non-conductive material is an electrically non-conductive ceramic material. Particularly preferably a carbide material, for example silicon carbide is used as such. In addition a combination of various materials, for example ceramic and polymer, is preferred. That is achieved for example by applying to a tube comprising a first material, one or more screw flights comprising a second material, for example by means of bonding, force-locking connection or positively locking connection, preferably for example by means of adhesive and/or screwing.

In a further preferred embodiment of the invention the electrode body is molded into the hollow shaft. Preferably the electrode body is epoxy resin-molded.

It is also preferred in accordance with the invention if the electrode body is surrounded in the hollow shaft by an insulating oil. The hollow shaft is filled up for example with an insulating oil, also referred to as transformer oil. The insulating oil is preferably an in particular highly refined mineral oil or a silicone oil.

Besides a device in accordance with the above-described embodiments the invention also concerns an installation for the production of a feed intermediate, comprising an inlet for the supply of material containing cell structures, and an outlet for discharge of the treated material as the intermediate product. In such an installation the invention attains its object in that the installation has a device for the electrical disintegration of cell structures, which is designed in accordance with one of the above-described preferred embodiments, being arranged downstream of the inlet and upstream of the outlet, receiving the material coming from the direction of the inlet and discharging it again in the direction of the outlet. In regard to the advantages and effects of the electrical disintegration device according to the invention attention is directed to the foregoing description.

In a preferred development of the installation according to the invention it has a moistening device for pre-conditioning, preferably by means of saturated steam, of the supplied material. Preferably the electrical disintegration device is arranged downstream or upstream of the moistening device. In pre-conditioning of the material containing cell structures heat and water vapour, preferably avoiding condensate, is supplied to the material containing cell structures. That has the advantage that the specific energy requirement per kilogram of material is reduced, or the through-put capacity can be increased with the same energy requirement. If the electrical disintegration device is arranged upstream of the moistening device then water absorption of the material containing cell structures is increased, following the flow through the electrical disintegration device. If the electrical disintegration device is arranged downstream of the moistening device then the already increased temperature and moisture loading of the material containing cell structures provide for a higher disintegration rate.

A further advantage of pre-conditioning of the material containing cell structures, with heat and vapour, is a reduction in the microbial loading of the product and an increase in digestibility. If the intermediate product is to be later still further processed, for example if it is to be pressed to form pellets, the strength of those pellets is later potentially increased and thus abrasion wear of the pellets upon conveying and transportation thereof is reduced.

In a further preferred embodiment the installation according to the invention has a treatment device for thermal and/or mechanical break-up of the supplied material, wherein the electrical disintegration device is preferably arranged upstream or downstream of the treatment device. For thermal and mechanical break-up it is possible for example to use an extruder which for example with the supply of heat circulates the product conveyed therein and subjects it to high shear loadings.

A preferred alternative to thermal and mechanical treatment by means of extruders is for example an expander for pressure conditioning of the material containing cell structures. Extruders and expanders have in common the fact that the conveyed product is subjected to thermal/mechanical break-up therewith. That manifests itself in a structural change in the material. When conveying for example whole grain that manifests itself in gelatinisation of the starch granules, higher fat availability, reduced germ content, breakdown of digestion-inhibiting substances and improved processing properties of the conveyed material.

The fact that the starch granules are split up permits reaction of the starch to form starch decomposition products like for example dextrins and maltose. Protein unfolding is further made possible.

After leaving the extruder or expander the intermediate product obtained is preferably cooled down before being further processed to form a further feed product, for example in an installation in accordance with the aspect described hereinafter. Optionally however the cooled intermediate product is alternatively or additionally also a preferred marketable product which then has to be mixed with water by the customer and can then be put to use.

In a further aspect the invention also concerns an installation for producing a pellet-form feed product and the installation in accordance with the invention includes the above-described installation for production of a feed intermediate in accordance with one of the above-described embodiments, and a pelleting device which is adapted to receive the intermediate product supplied thereto from the installation for production of the feed intermediate, process it to form pellets, in particular pressing it, and discharge it as a pellet-form feed product. In regard to the advantages of that installation attention is directed to the foregoing description relating to the device according to the invention for the disintegration thereof.

Besides the electrical disintegration device itself and the installations using same in a further aspect the invention also concerns the use of a device for electrical disintegration in the production of a feed intermediate, wherein the electrical disintegration device has a chamber having an inlet for receiving material containing cell structures, an outlet for the discharge thereof, and a conveyor line extending between the inlet and the outlet, as well as an electrode unit having an electrode body which is arranged within the chamber at least portion-wise along the conveyor line, wherein the chamber has a wall which is portion-wise or completely electrically conductive and is electrically insulated from the electrode body, and the electrode unit is adapted to generate an electric field for electrical disintegration between the electrode body and the wall. In particular the invention concerns such a use of the above-indicated kind, in which a conveyor screw for conveying the material is driveably arranged in the conveyor line of the electrical disintegration device, the electrode body being accommodated in a cavity in the conveyor screw.

In preferred developments of the use according to the invention the electrical disintegration device is in accordance with one of the foregoing embodiments described herein.

In a further aspect the invention also concerns the use of a device for electrical disintegration in the production of a feed product, wherein the electrical disintegration device is preferably also designed as was already described hereinbefore with reference to the use for the production of a feed intermediate.

The device according to the invention was described hereinbefore in relation to its preferred suitability for the electrical disintegration of material containing cell structures. Besides its suitability and use for that purpose however the device is also particularly suitable for modifying the surface charge of particles. Thus in a further aspect the invention concerns a device for the electrical modification of the surface charge of particles, comprising a chamber having a material inlet, a material outlet and a conveyor line extending between the material inlet and the material outlet, an electrode unit having an electrode body which is arranged within the chamber at least portion-wise along the conveyor line, wherein the chamber has a wall which is portion-wise or completely electrically conductive and is electrically insulated from the electrode body, and wherein the electrode unit is adapted to generate an electric field for modification of the surface charge between the electrode body and the wall, wherein a conveyor screw for conveying the material is driveably arranged in the conveyor line, the electrode body being accommodated in a cavity in the conveyor screw.

The device is structurally identical therefore to the above-described device for the electrical disintegration of material containing cell structures, with the exception that in operation it is not material containing cell structures but a particle-bearing material that is introduced into the chamber and discharged again therefrom. According to the invention the term particles is used to mean dispersed materials which differ from the converted continuous medium by a phase boundary interface. That can be for example the solid or liquid components of aerosols, the solid components of suspensions, the particles of powders, or also liquid drops in emulsions. By modifying the surface charge of the particles substances which involve static repulsion in the untreated state can be better processed after passing through the apparatus for electrical modification of the surface charge, for example in mixing apparatuses. That can be applied for example in relation to fluid containing oil droplets, paints or suspensions of starch powders.

The device for the electrical modification of the surface charge of particles involves the same realisations and advantages as the above-described electrical disintegration device and has the same preferred embodiments, for which reason attention is directed in that respect to the foregoing description.

Therefore besides a use of the described device for the electrical disintegration of material containing cell structures the invention also concerns the use of the apparatus for the electrical modification of the surface charge of particles, the apparatus being in accordance with one of the preferred embodiments described herein.

Figure 2:
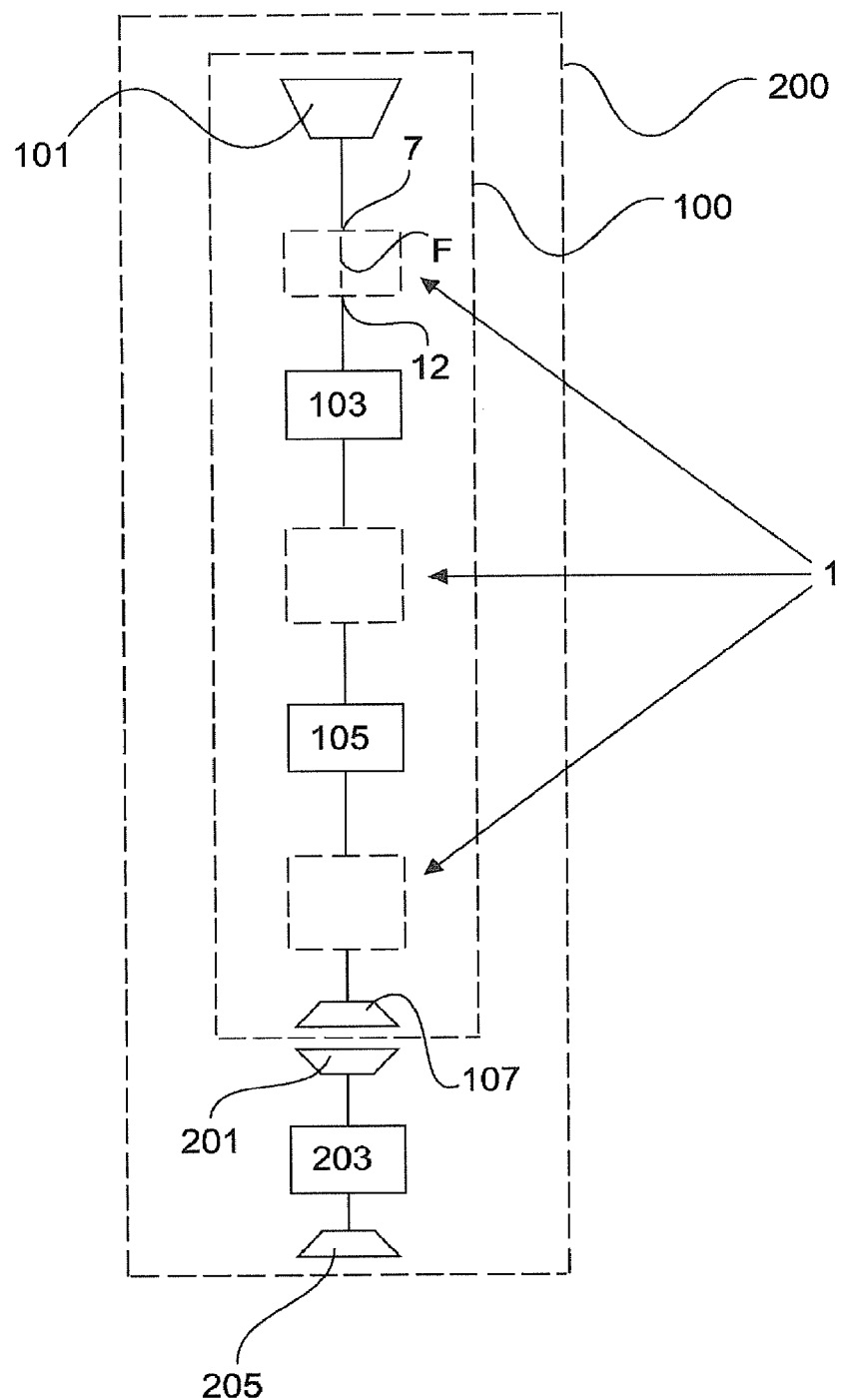

The invention is described in greater detail hereinafter by means of preferred embodiments by way of example with reference to the accompanying Figures in which:

FIG. 1 shows an electrical disintegration device according to a preferred embodiment, and FIG. 2 is a diagrammatic view showing the structure of an installation for the production of a feed product in accordance with a preferred embodiment.

The diagrammatic structure of the electrical disintegration device according to invention is shown in partial section in FIG. 1. The electrical disintegration device 1 has a main body 3. The main body 3 is grounded. Arranged on the main body 3 is a first connection 5 which has an inlet 7 for the introduction into the device 1 of material containing cell structures or particles. Also arranged on the main body 3 is a second connection 9 having an outlet 12 for discharge of the previously introduced material. Extending between the inlet 7 and the outlet 12 is a conveyor line, identified by a broken line F. In an alternative configuration (not shown here) the electrode unit and the drive are preferably arranged in the reverse sequence.

Provided in the interior of the main body 3 is a chamber 5, through which the material containing particles or cell structures is conveyed. The chamber has a conveyor screw 14. The conveyor screw 14 has a plurality of conveyor flights 16 which bear with as little play as possible against a wall 19 of the chamber 5 to ensure conveyance, with as low a degree of return flow as possible, of the material containing particles or cell structures. The conveyor flights 16 are disposed on a hollow shaft 18. The conveyor screw 14 is preferably driveable or controllable by means of an electric-motor drive 20. Alternative kinds of drive are preferably hydraulic drives, gas motors or mechanical drives (for example belt drives).

The device 1 further has an electrode unit 11 which includes an electrode head 13 and an electrode body 15, the electrode body 15 being arranged within the chamber 5 along the conveyor line F. The electrode unit 11 is grounded. The electrode body 15 is accommodated within the hollow shaft 18. The electrode unit is actuated by a control unit 21. The control unit is preferably designed in principle as described in DE 20 2013 009 847.

In operation an electric field is generated by means of the electrode unit 11 within the chamber 5 between the electrode body 15 and the wall 19 of the chamber. The electric field acts on the material containing cell structures conveyed along the conveyor line F, or on the particles conveyed along the conveyor line F, and with an adequate field strength, in the case of the material containing cell structures, leads to electroporation or electrical disintegration of cell structures or, in the case of the material containing particles, it leads to an electrical modification in the surface charge, in particular a discharge. It is also possible that the surface charge is modified in the case of the material containing cell structures in a similar way to the case with the particles, thereby affording improved disintegration. That is considered in the case of material containing cell structures in particular when it is arranged between an inlet 101 and a moistening device 103 of an installation 200 for producing feed intermediates or feed products (see FIG. 2). The water absorption rate (wetting of the particles) can be increased by that arrangement and that then involves a higher level of specific energy liberation upon extrusion/expansion.

The operator can exactly determine the residence time of the material containing particles or cell structures (for example whole grain, pre-conditioned whole grain or whole grain which has already been thermally and mechanically broken up) by way of the speed of rotation of the conveyor screw 14. That advantageously guarantees treatment of the material supplied by the inlet 7, that is matched to the field strength, the material containing particles or cell structures to be conveyed and the desired effect, in optimum fashion and reproducibly with a high level of accuracy.

In a preferred configuration the device 1 for electrical disintegration can be provided in installations for the production of feed intermediates or feed products at various locations alternatively or cumulatively in order there to subject the material containing the respectively conveyed cell structures to electrical disintegration in specifically targeted fashion. Types of installation by way of example are shown in FIG. 2.

FIG. 2 diagrammatically shows an installation 200 for the production of a feed product. The installation 200 also includes an installation 100 for the production of a feed intermediate.

The installation 100 has an inlet 101 for the feed of material containing cell structures, for example whole grain. In addition the installation 100 has an outlet 107 for discharge of the treated material as an intermediate product. A component part of the installation 100 is a moistening device 103 for pre-conditioning the material. Material containing cell structures coming from the inlet 101 is supplied to the moistening device 103 and is then discharged again in the direction of the outlet 107. Provided downstream of the moistening device 103 is a treatment device 105 to which the pre-conditioned material containing cell structures is supplied for thermal and/or mechanical break-up. Preferably the treatment device has an extruder and/or expander.

The installation 100 has at least one electrical disintegration device 1. The device is preferably arranged upstream or downstream of the moistening device 103 and/or upstream or downstream of the treatment device 105. Alternatively it is also preferred to provide more than one electrical disintegration device 1 in the installation 100. Depending on the location at which the electrical disintegration device 1 is disposed in the installation 100 between the inlet 101 and the outlet 107 it receives the material which contains cell structures and which is in its respective state, subjects it to electrical disintegration and then discharges it again to the following processing step or the outlet 107 (in the case in which the electrical disintegration device 1 is provided at the location that is downward in FIG. 2).

The installation 100 in FIG. 2 is a component part of the installation 200 for producing the feed product. In the present case the installation 200 is an installation for producing a pellet-form feed product. In addition to the installation 100 for producing the feed intermediate the installation 200 also includes a pelletting device 203. By way of an inlet 201 the pelletting device 203 receives the feed intermediate which is discharged by the installation 100. That can take place directly, or by the interposition of suitable transport means. Storage of the feed intermediate possibly also takes place before it is supplied to the pelletting device 203 through its inlet 201. After the pelletting operation the pelletting device 203 discharges the finished feed product in pellet form through an outlet 205.

As was explained in detail hereinbefore the invention in an aspect provides the feed industry involving electrical disintegration with an innovative resource with which feed exploitation and usage is further improved in relation to the energy expenditure necessary for production thereof. Electrical disintegration devices can be advantageously used both in the production of feed intermediates and also in the production of finished feed products.

In a further aspect the invention involving substantially the same apparatus structure affords a tool for electrical modification of the surface charge of material containing particles, which improves the processability of the particle-containing material.

The invention claimed is:

1. A device for the electrical disintegration of cell structures, comprising:
a chamber having an inlet for receiving material containing cell structures, an outlet for the discharge thereof, and a conveyor line extending between the inlet and the outlet,
an electrode unit which has an electrode body which is arranged within the chamber at least partially along the conveyor line, wherein:
the chamber has a chamber wall which is partially or completely electrically conductive;
the electrode unit is adapted to generate an electric field between the electrode body and the wall for electrical disintegration; and
a conveyor screw is arranged driveably in the conveyor line for conveying the material, wherein the electrode body is accommodated in a cavity in the conveyor screw, such that the chamber wall is electrically insulated from the electrode body,
wherein the conveyor screw has a hollow shaft and the electrode body is arranged coaxially with the conveyor screw in the hollow shaft, and
wherein the conveyor screw partly or completely comprises electrically non-conductive material.

2. A device as set forth in claim 1, wherein an electrically non-conductive, organic, polymer is used as the electrically non-conductive material.

3. A device as set forth in claim 1, wherein the electrically non-conductive material is an electrically non-conductive ceramic material.

4. A device as set forth in claim 1, wherein the conveyor screw comprises two or more different electrically non-conductive materials an electrically non-conductive, organic, polymer and an electrically non-conductive ceramic material.

5. A device as set forth in claim 1, wherein the electrode body is molded into the hollow shaft, epoxy resin molded.

6. A device as set forth in claim 1, wherein the electrode body is surrounded in the hollow shaft by an insulating oil.

7. A device as set forth in claim 6, wherein the insulating oil is a mineral oil or a silicone oil.

8. A device for the electrical modification of the surface charge of particles, comprising:
a chamber having a material inlet, a material outlet and a conveyor line extending between the material inlet and the material outlet;
an electrode unit which has an electrode body which is arranged within the chamber at least partially along the conveyor line;
wherein:
the chamber has a chamber wall which is partially or completely electrically conductive;
the electrode unit is adapted to generate an electric field for modification of the surface charge between the electrode body and the wall;
a conveyor screw is arranged driveably in the conveyor line for conveying the material, wherein the electrode body is accommodated in a cavity in the conveyor screw, such that the chamber wall is electrically insulated from the electrode body;
the conveyor screw has a hollow shaft and the electrode body is arranged coaxially with the conveyor screw in the hollow shaft; and the conveyor screw partly or completely comprises electrically non-conductive material.

9. Installation for producing a feed intermediate comprising:
an inlet for the feed of material containing cell structures,
an outlet for the discharge of the treated material as an intermediate product,
a device for the electrical disintegration of cell structures, which is designed as set forth in claim 1, being arranged downstream of the inlet and upstream of the outlet and receiving the material coming from the direction of the inlet and discharging same in the direction of the outlet.

10. Installation as set forth in claim 9, further comprising a steam-generator, wherein the device for electrical disintegration is arranged downstream or upstream of the steam generator.

11. Installation as set forth in claim 9, comprising a treatment device for thermal and/or mechanical break-up of the supplied material, wherein the device for electrical disintegration is arranged upstream or downstream of the treatment device.

12. Installation for the production of a pellet-form feed product comprising the installation for production of a feed intermediate as set forth in claim 9, and a pellet former.

13. A method for electrical disintegration in the production of a feed intermediate, the method comprising:
receiving material containing cell structures into an inlet of a chamber of a device, the chamber also comprising an outlet for the discharge thereof, and a conveyor line extending between the inlet and the outlet, the chamber having a chamber wall which is partially or completely electrically conductive; and
generating an electric field for the electrical disintegration via an electrode unit between an electrode body of the electrode unit, wherein the electrode unit is arranged within the chamber at least partially along the conveyor line and wherein the chamber wall is electrically insulated from the electrode body,
wherein a conveyor screw for conveying the material is driveably arranged in the conveyor line of the device for electrical disintegration, wherein the electrode body is accommodated in a cavity in the conveyor screw,
wherein the conveyor screw has a hollow shaft and the electrode body is arranged coaxially with the conveyor screw in the hollow shaft, and
wherein the conveyor screw partly or completely comprises electrically non-conductive material.

14. The method as set forth in claim 13, further comprising pre-conditioning the material using saturated steam.

15. The method as set forth in claim 13, further comprising:
receiving the feed intermediate;
pressing the received feed intermediate to form pellets; and
discharging the formed pellets as a pellet-form feed product.

16. A method for electrical disintegration in the production of a feed product, the method comprising: receiving material containing cell structures within an inlet of a chamber of a device, the chamber further comprising an outlet for the discharge thereof, and a conveyor line extending between the inlet and the outlet, wherein the chamber has a wall which is partially or completely electrically conductive; and
using an electrode unit to generate an electric field between an electrode body of the electrode unit and the wall for the electrical disintegration, wherein the electrode body is arranged within the chamber at least partially along the conveyor line and wherein the wall is electrically insulated from the electrode body,
wherein a conveyor screw for conveying the material is driveably arranged in the conveyor line of the device for electrical disintegration, wherein the electrode body is accommodated in a cavity in the conveyor screw,
wherein the conveyor screw has a hollow shaft and the electrode body is arranged coaxially with the conveyor screw in the hollow shaft, and
wherein the conveyor screw partly or completely comprises electrically non-conductive material.

17. The method as set forth in claim 16, further comprising pre-conditioning the material using saturated steam.

18. The method as set forth in claim 16, further comprising:
receiving the feed product;
pressing the received feed product to form pellets; and
discharging the formed pellets as a pellet-form feed product.

19. A method for the electrical modification of the surface charge of particles, the method comprising:
receiving material within the material inlet of the chamber of the device set forth in claim 8;
generating the electric field using the electrode unit; and
using the conveyor screw to convey the material toward the material outlet.

\* \* \* \* \*